(12) United States Patent
Dann

(10) Patent No.: US 10,226,557 B2
(45) Date of Patent: Mar. 12, 2019

(54) BREAST MILK COLLECTION DEVICES AND METHODS THEREOF

(71) Applicant: Kristin Dann, Portland, OR (US)

(72) Inventor: Kristin Dann, Portland, OR (US)

(73) Assignee: Bond and Love, LLC, Keizer, OR (US)

( * ) Notice: Subject to any disclaimer, the term of this patent is extended or adjusted under 35 U.S.C. 154(b) by 434 days.

(21) Appl. No.: 15/143,257

(22) Filed: Apr. 29, 2016

(65) Prior Publication Data
US 2016/0331879 A1    Nov. 17, 2016

Related U.S. Application Data

(60) Provisional application No. 62/160,189, filed on May 12, 2015.

(51) Int. Cl.
*A61M 1/06* (2006.01)

(52) U.S. Cl.
CPC ............ *A61M 1/066* (2014.02); *A61M 1/064* (2014.02)

(58) Field of Classification Search
CPC .......... A61J 9/005; A61M 1/06; A61M 1/062; A61M 1/064; A61M 1/066
See application file for complete search history.

(56) References Cited

U.S. PATENT DOCUMENTS

| | | | |
|---|---|---|---|
| 1,032,518 A | 7/1912 | Thieringer | |
| 6,887,218 B2 * | 5/2005 | Warburton | A61M 1/066 604/74 |
| 7,472,797 B2 | 1/2009 | Ostrowski | |
| 7,806,855 B2 * | 10/2010 | Kliegman | A61M 1/06 604/73 |
| 8,444,596 B2 | 5/2013 | Paterson et al. | |
| 8,469,771 B2 | 6/2013 | Francis | |
| 2004/0024351 A1 * | 2/2004 | Greter | A61M 1/0037 604/74 |
| 2004/0094498 A1 * | 5/2004 | Foley | A61J 9/001 215/11.3 |
| 2007/0022961 A1 | 2/2007 | Wheeler | |

(Continued)

OTHER PUBLICATIONS

Philips Avent Nipple Protectors SCF156 Standard, http://www.p4c.philips.com/cgi-bin/dcbint/cpindex.pl?ctn=SCF156/01&scy=us&slg=en, 2009.

*Primary Examiner* — Imani N Hayman
*Assistant Examiner* — Tiffany Legette
(74) *Attorney, Agent, or Firm* — Lempia Summerfield Katz LLC

(57) ABSTRACT

The disclosure provides embodiments for collecting breast milk (such as colostrum). Collection devices for collecting the breast milk include a breast shield having a first open end, a second open end, and a breast covering material positioned between the first open end and the second open end, wherein an interior surface of the breast shield is configured to abut a portion of a breast inserted through the first open end, wherein the second open end is configured to surround a nipple of the breast, and wherein a diameter of the second open end is less than a diameter of the first open end. The devices further include a collection tube having an open end and a closed end, wherein the open end of the collection tube is configured to connect with the second open end of the breast shield.

18 Claims, 5 Drawing Sheets

(56) References Cited

U.S. PATENT DOCUMENTS

2010/0193460 A1\* 8/2010 Driver ................. A61J 9/001
 215/11.3
2013/0281983 A1\* 10/2013 Sherman ............... A61M 1/06
 604/514
2014/0052106 A1 2/2014 Sherman \* cited by examiner

BREAST MILK COLLECTION DEVICES AND METHODS THEREOF

This application claims the benefit of U.S. Provisional Application No. 62/160,189, filed on May 12, 2015, which is hereby incorporated by reference in its entirety.

FIELD

The following disclosure relates to breast milk collection devices and methods thereof. More specifically, the following disclosure relates to devices and methods for collecting colostrum.

BACKGROUND

Colostrum or "first milk" is a form of milk produced by the mammary glands of mammals in late stage of pregnancy, such as just prior to giving birth, and sometimes even after pregnancy. Colostrum is the first nutritional liquid that comes out of the breast during lactation. Colostrum may include antibodies to protect the newborn against disease, and may be lower in fat and higher in protein than ordinary breast milk.

Colostrum is produced at a slow rate of several milliliters per hour and may require some form of pumping and/or hand expression to cause the liquid to exit the breast. In the first few days after birth, a newborn may be breastfed numerous times every day (e.g., 8-12 times per day). This allows the baby to get the benefits of the colostrum while stimulating production of mature milk.

Collection of breast milk (e.g., colostrum) may be difficult, due to the small amount of volume produced initially following giving birth. Existing breast milk pumps may not be designed for the small volumes initially expressed from the breast. Besides breast pumps, the generally accepted practice is to use whatever container is available to collect the initial breast milk. These containers may require transfer to another container for administering. Such a transfer of material may lead to loss of the initial breast milk when every precious drop counts.

Currently used techniques and devices for collecting and administering initial breast milk (e.g., colostrum) have a number of drawbacks. For example, current techniques may involve expressing colostrum into a relatively large container, such as a plastic cup or breast pump bottle. As the colostrum or initial mature milk may be produced in small volumes, mothers may often get discouraged when the colostrum appears to be incredibly small-volume relative to a large container. This may cause a mother to give up on breast-feeding during the first few days of a newborn's life.

Therefore, it is desirable to provide improved devices, systems, and methods for collecting colostrum or initial mature milk from a breast and storing and/or dispensing the colostrum. The devices, devices, and methods may be designed to transfer colostrum or breast milk to the newborn in an efficient way, so that very little colostrum or breast milk is lost in the process.

SUMMARY

The disclosure provides embodiments for collecting breast milk (e.g., colostrum). In one embodiment, a collection device is provided. The collection device includes a breast shield having a first open end, a second open end, and a breast covering material positioned between the first open end and the second open end, wherein an interior surface of the breast shield is configured to abut or touch a portion of a breast inserted through the first open end, wherein the second open end is configured to surround a nipple of the breast, and wherein a diameter of the second open end is less than a diameter of the first open end. The collection device further includes a collection tube having an open end and a closed end, wherein the open end of the collection tube is configured to connect with the second open end of the breast shield. The collection device is configured to collect breast milk in the collection tube through stimulation of the nipple.

In another embodiment, a collection tube is provided. The collection tube is configured to attach to a breast shield having a first open end, a second open end, and a breast covering material positioned between the first open end and the second open end. The collection tube includes an open end and a closed end, wherein the open end of the collection tube is configured to attach to and detach from the second open end of the breast shield. The collection tube is configured to collect breast milk when attached to the breast shield through stimulation of the nipple.

In another embodiment, a method is provided for collecting breast milk (e.g., colostrum). The method includes placing a collection device over a nipple of a breast, the collection device having (1) a breast shield having a first open end, a second open end, and a breast covering material positioned between the first open end and the second open end, wherein an interior surface of the breast shield abuts or touches a portion of the breast and the second open end is surrounds the nipple of the breast, and (2) a collection tube having an open end and a closed end, wherein the open end of the collection tube is connected to the second open end of the breast shield. The method further includes expressing breast milk from the nipple. The method further includes collecting the breast milk in the collection tube of the collection device. The method further includes removing the collection device from the nipple of the breast.

BRIEF DESCRIPTION OF THE DRAWINGS

Exemplary embodiments are described herein with reference to the following drawings.

DETAILED DESCRIPTION

As used herein, the term "breast milk" may refer to colostrum, transitional milk, and/or mature milk. Colostrum is the first stage of breast milk that occurs during pregnancy and lasts for several days after the birth of the baby. Colostrum is high in protein, fat-soluble vitamins, minerals, and immunoglobulins. Transitional milk occurs after colostrum and may last for approximately two weeks. Transitional milk includes high levels of fat, lactose, water-soluble vitamins, and contains more calories than colostrum. Mature milk is the final milk produced, and is approximately 90% water and 10% carbohydrates, proteins, and fats.

As described in further detail below, devices and methods are provided for improving the collection of breast milk such as colostrum. For example, devices are provided to collect and retain a higher percentage of the small amount of breast milk (e.g., colostrum) produced shortly after childbirth. The improved collection device includes a breast shield attached to a collection tube with a closed end to retain the breast milk.

Collection Devices

Figure 1:
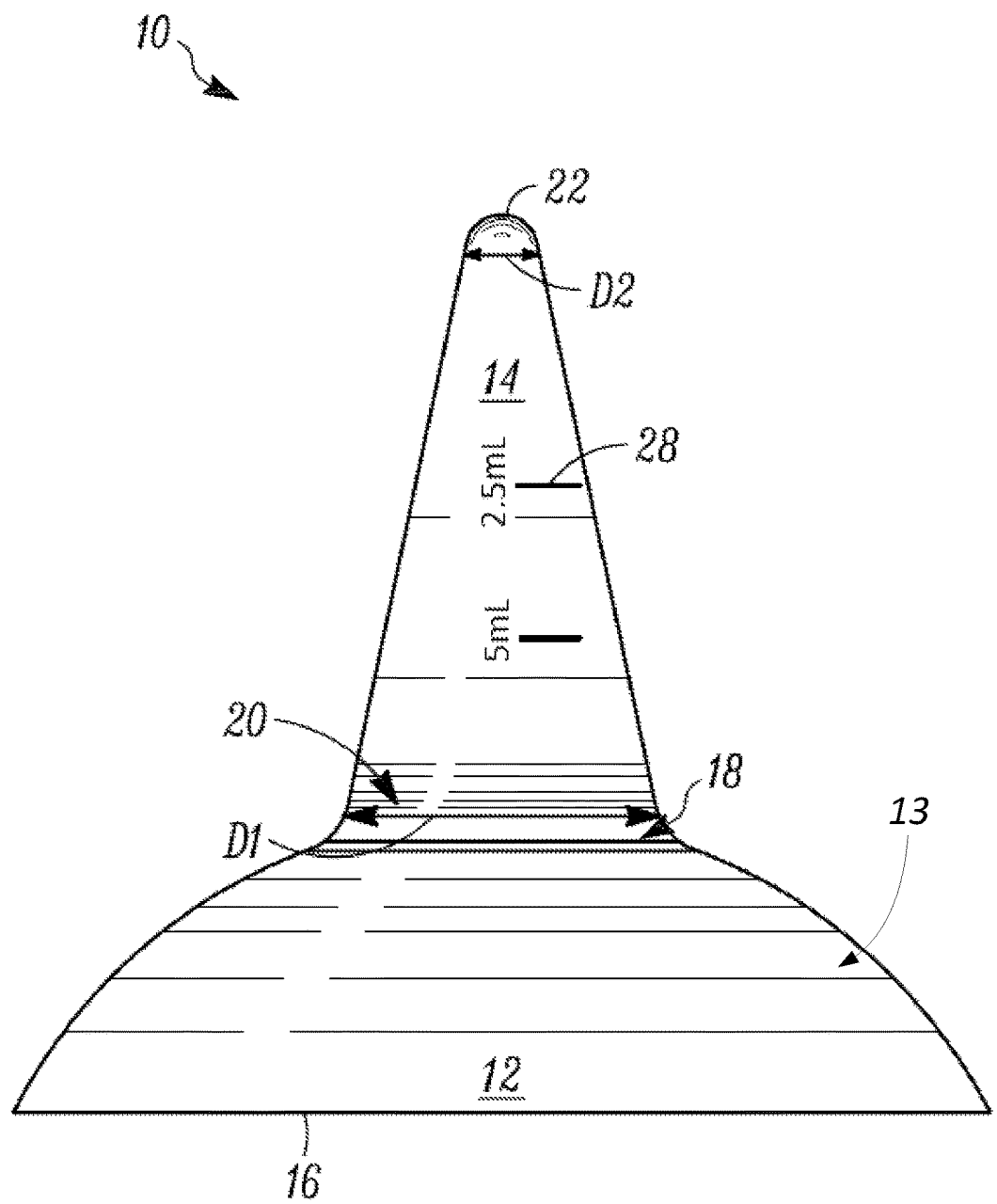
FIG. 1 depicts an example of a device for collecting breast milk (e.g., colostrum).
Figure 2:
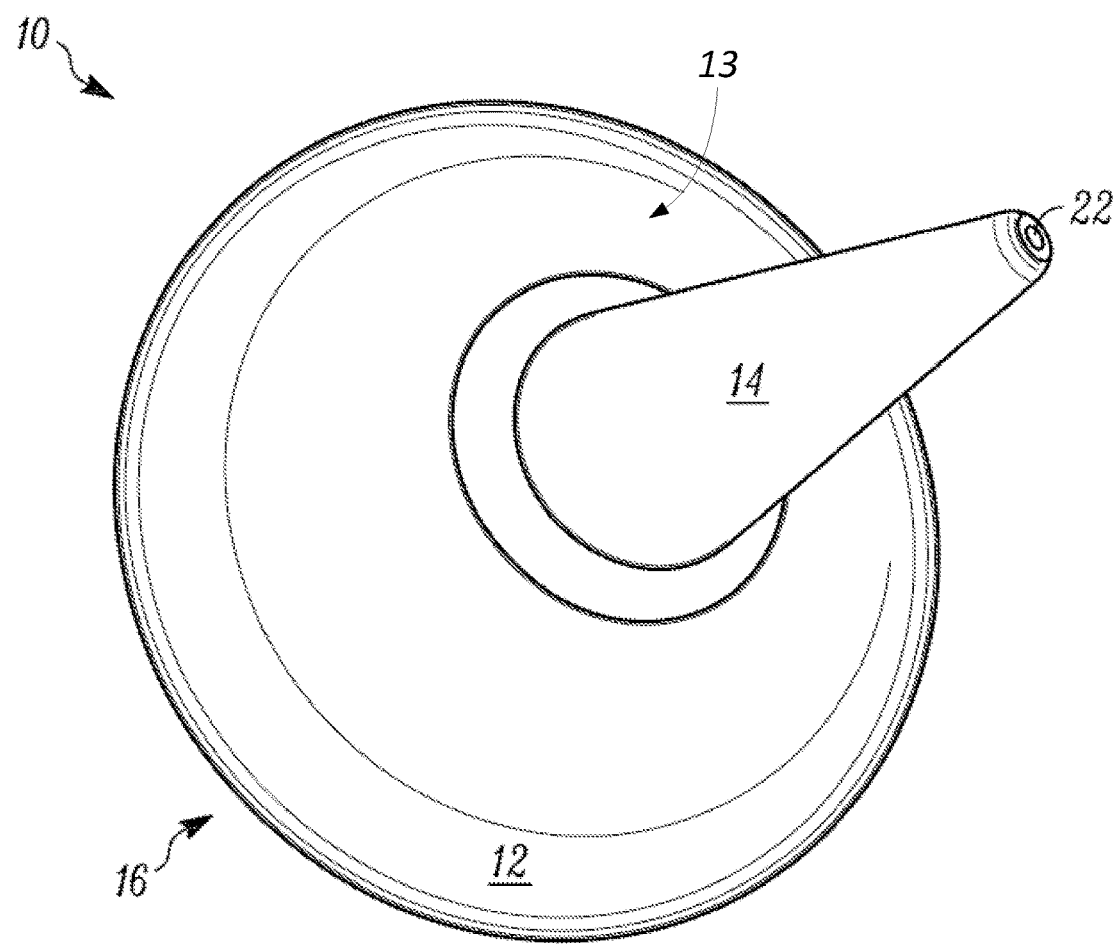
FIG. 2 depicts an additional view of the example of the device in FIG. 1.

FIG. 1 depicts one example of a breast milk collection device 10 configured to collect breast milk. FIG. 2 depicts a separate angle of the collection device 10. The device 10 may collect the breast milk through stimulation of the nipple. The device 10 includes a breast shield 12 connected to a collection tube 14. The breast shield 12 includes a first open end 16 and a second open end 18, opposite the first open end 16. A covering material 13 is positioned between the two open ends of the breast shield 12. In certain examples, the diameter of the second open end is less than the diameter of the first open end.

The breast shield 12 may be configured such that a portion of the breast inserted through the first open end 16 abuts or touches the interior surface of the breast shield. The breast shield 12 may also be configured such that the nipple of the breast is aligned with the second open end 18, wherein the second open end 18 surrounds the nipple.

The collection tube 14 includes an open end 20 and a closed end 22. The open end 20 of the collection tube 14 is configured to connect with the second open end 18 of the breast shield 12. The closed end 22 is configured to retain the collected breast milk. In certain examples, the collection tube 14 and breast shield 12 are centered about an axis running through the collection device 10 from the first open end 16 of the breast shield 12 through the closed end 22 of the collection tube 14.

In certain examples, the shape of the collection tube 14 is cylindrical, conical, or a combination thereof. For example, the shape may be a cylinder, wherein the cylinder includes a height between the open end 20 and the closed end 22 of the collection tube 14, a first diameter D1 at the open end of the collection tube 14, and a second diameter D2 at the closed end of the collection tube 14, wherein the first diameter and the second diameter are equal.

In another example, the collection tube 14 is a cone where the closed end of the tube is the apex of the cone. In yet another example, the shape of the collection tube 14 is a conical frustum having a height between the open end 20 and the closed end 22 of the collection tube 14, wherein a diameter D1 at the open end 20 of the collection tube 14 is greater than a diameter D2 at the closed end 22 of the collection tube 14. In certain examples, the shape of the collection tube 14 may have properties attributed to both a cone and a cylinder. For example, the collection tube 14 may be cylindrical at the open end 20 of the tube and transition to a conical shape ending at an apex or frustum at the closed end 22 of the tube 14.

The volume of the collection tube 14 is variable. In certain examples, the collection tube 14 may have a volume of 1-5 milliliters (mL), 5-10 mL, 10-15 mL, 15-25 mL, or 25-50 mL. In certain examples, the height of the collection tube 14 is less than the diameter of the first open end of the breast shield 12. In alternative examples, the height of the collection tube 14 is greater than the diameter of the first open end of the breast shield 12.

In certain examples, the collection device 10 is made out of a flexible material that is configured to be inverted, wherein the closed end 22 of the collection tube 14 is moved through the first open end 16 of the breast shield to expose an interior surface of the collection tube 14 and the interior surface of the breast shield 12. By inverting the collection device 10, leftover drops of breast milk stuck to walls of the collection tube 14 may be exposed for easier access (e.g., with a finger).

The flexible material of the collection device 10 may be a plastic composition. The flexible material may be formed from one or more polyolefin polymers. The composition may include one or more of the following polymers: polyurethane, nylon, polyethylene, polyvinyl chloride, and combinations thereof. In some examples, the composition of the breast shield 12 is the same as the composition of the collection tube 14. In other examples, the breast shield 12 and collection tube 14 are made from different compositions.

The collection tube 14 may be made of a material that is at least partially transparent, such that the breast milk collected within the collection tube 14 may be visible from the outside of the collection tube 14. Additionally, in some examples, one or more marker indications 28 may be located on the outer surface of the collection tube to indicate the volume of breast milk collected. The number and/or spacing of marker indications 28 is configurable based on the volume of the collection tube.

In certain examples, the collection tube 14 is attachable and detachable from the breast shield 12. In such examples, different sized breast shields may be interchanged to accommodate different breast sizes and shapes, while maintaining the same collection tube 14 attachment. In some examples, the collection tube 14 is configured to attach to a commercially available breast or nipple shield.

Figure 3:
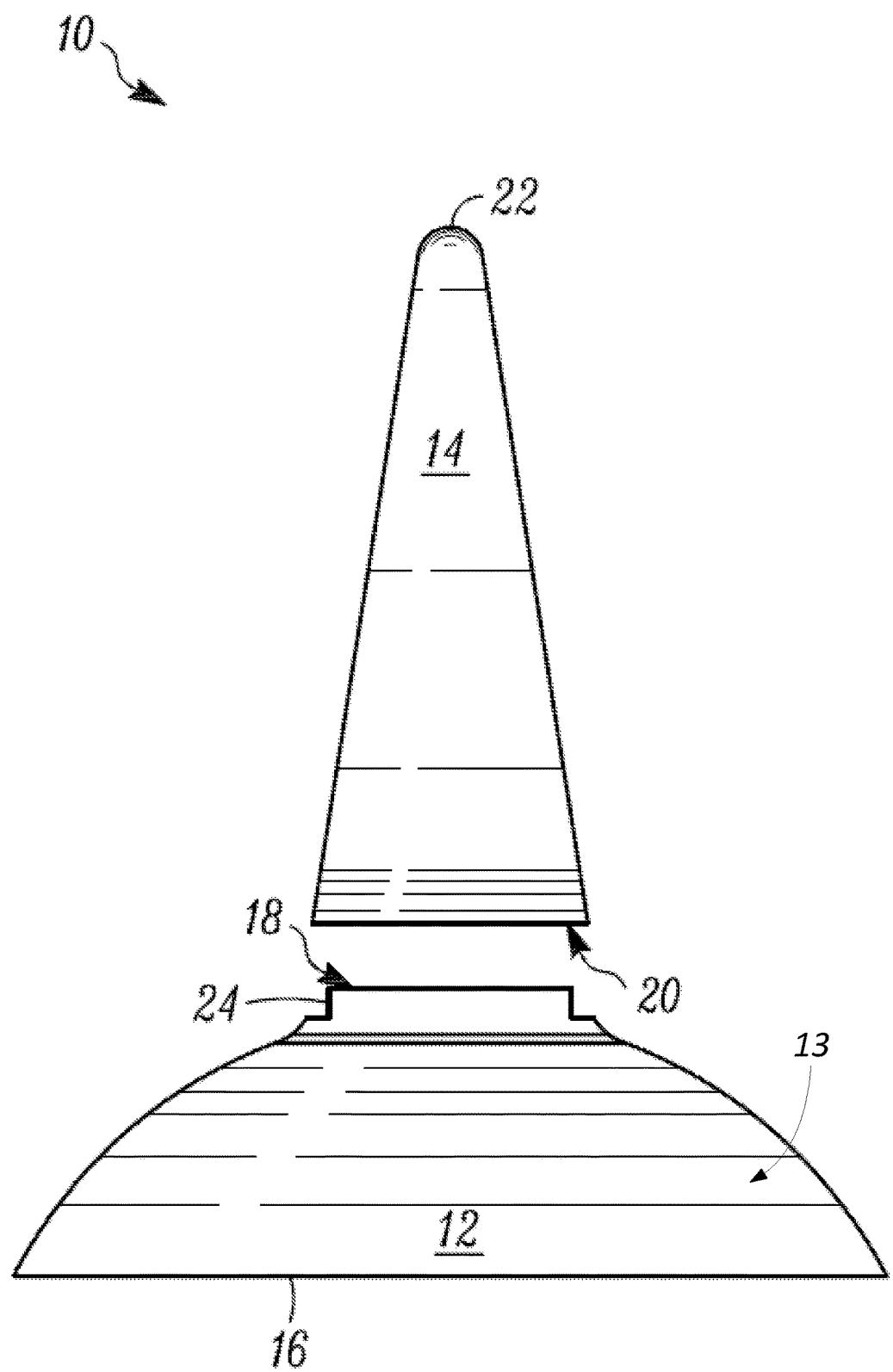
FIG. 3 depicts an example of a collection device having a detachable collection tube.

FIG. 3 depicts one example of a detachable/attachable arrangement between the collection tube 14 and the breast shield 12. As depicted in FIG. 3, the breast shield 12 includes, at the second open end 18, a ring-shaped projection 24 having an external surface. The ring-shaped projection 24 is configured to connect with or abut a portion of an internal surface of the collection tube 14 at the open end 20 of the collection tube 14 when attached to the breast shield 12.

In certain examples, the collection tube 14 may be attached and detached from the breast shield 12 through a form-fit arrangement wherein the open end 20 of the collection tube 14 is stretched around the outer surface of the ring-shaped projection 24. In other examples, the collection tube 14 may have a threaded surface, and the ring-shaped projection 24 may have a corresponding, opposite threaded surface, wherein the collection tube 14 is screwed onto or into the ring-shaped projection 24. In one example, the external surface of the ring-shaped projection 24 is threaded and a portion of the internal surface of the collection tube 14 is threaded such that the collection tube 14 is configured to screw over the outer surface of the ring-shaped projection 24. In an alternative example, the internal surface of the ring-shaped projection 24 is threaded and a portion of the external surface of the collection tube 14 is threaded such that the collection tube 14 is configured to screw into the inside of the ring-shaped projection 24.

In certain examples, the detached collection tube 14 may be made out of a flexible material that is configured to be inverted. The tube 14 may be inverted or flipped inside out by moving the closed end of the collection tube 14 through the open end of the collection tube 14 to expose the interior surface. By inverting the tube 14, leftover drops of breast milk stuck to walls of the tube may be exposed for easier access (e.g., with a finger).

In certain examples, a safety lid may be provided for the detached collection tube 14. The safety lid may be screwed, snapped, or affixed onto the open end of the collection tube 14 when the collection tube 14 is detached from the breast shield. In such an example, the collection tube 14 may be used as a storage container for retaining the breast milk for use at a later time.

Collection System

In certain examples, breast milk may be collected in the collection tube through stimulation of the nipple. For example, the nipple may be stimulated through manual expression of the nipple. In other examples, the breast milk is collected in the collection tube with assistance from a breast pump, wherein the breast pump is placed over the collection device attached to the breast. The breast pump may use suction to pull a partial vacuum within the collection tube, wherein breast milk is stimulated to flow into the tube through a pressure gradient. Alternatively, or additionally, the breast pump may be configured to massage the nipple to express the breast milk. Massaging may include a breast pump having a variable vibration mechanism surrounding the nipple to gently squeeze or shake the nipple to stimulate the breast milk.

Figure 4:
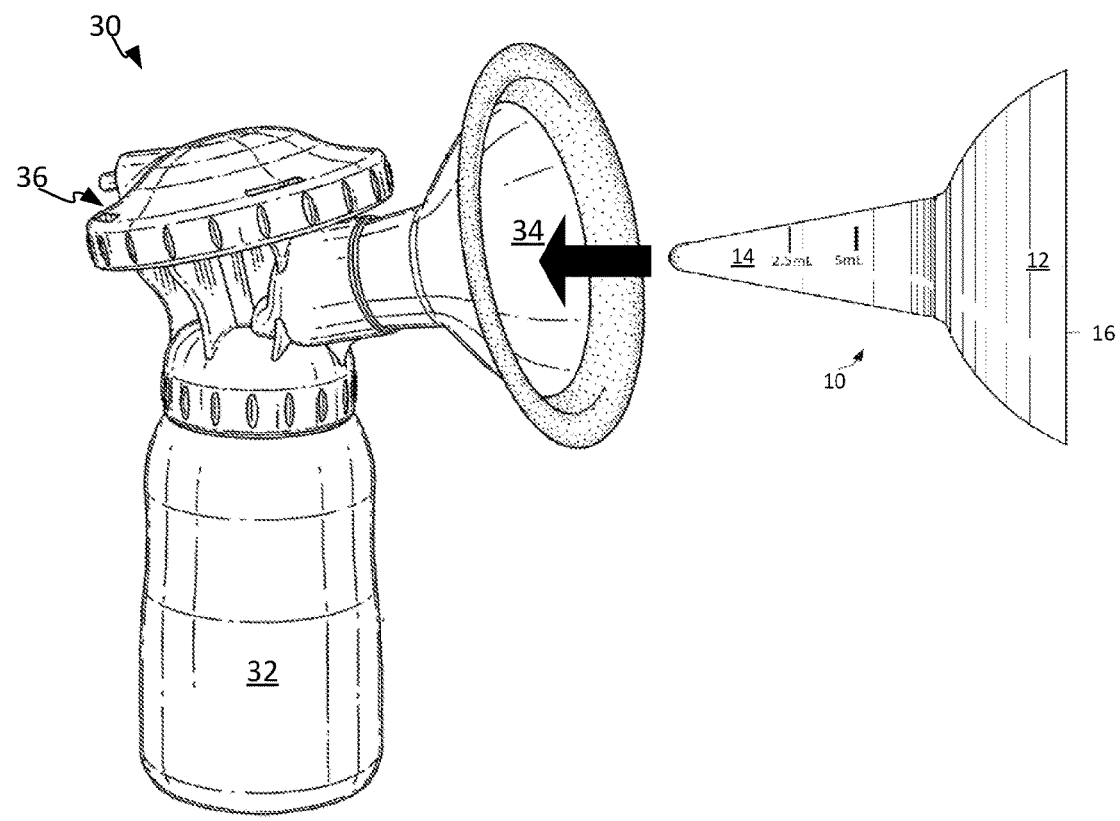
FIG. 4 depicts an example of a breast pump configured to interact with a collection device to collect breast milk.

FIG. 4 depicts one example of a breast pump 30 for expressing milk with the collection device. The breast pump 30 may include a collection bottle 32, which would not be in use since the collection tube is attached and has a closed end preventing flow of breast milk into the collection bottle. The breast pump 30 also may include a breast shield 34 for placement of the breast. Additionally, the breast pump 30 may include a suction transfer apparatus 36 connected to a vacuum pump by a tube. The suction transfer apparatus 36 may be constructed such that it transfers vacuum through a deformable diaphragm. By pulling a vacuum through the suction transfer apparatus 26, the nipple may be expressed, allowing breast milk (e.g., colostrum) to be generated.

Flowchart Embodiments

Figure 5:
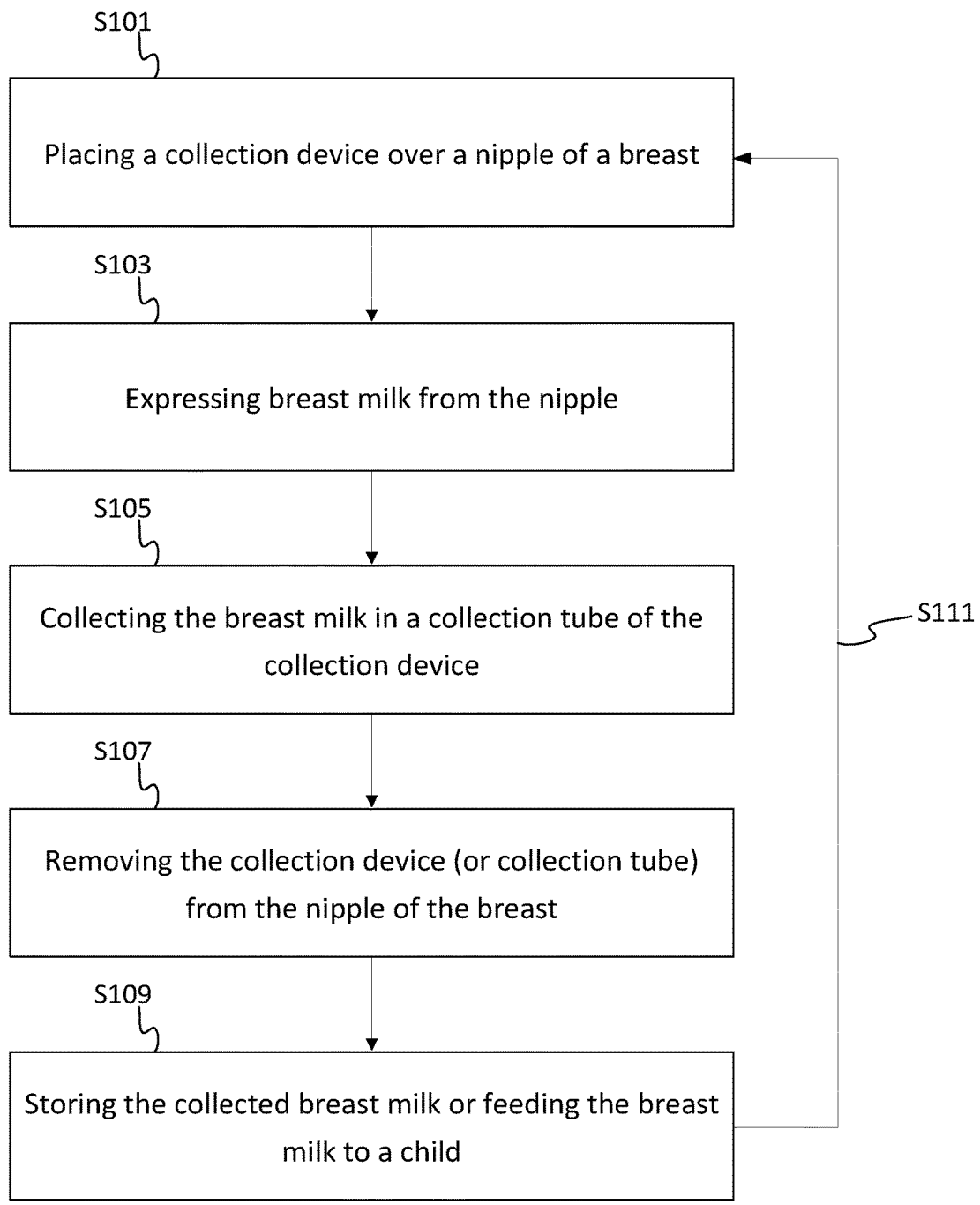
FIG. 5 illustrates an example flowchart for collecting breast milk.

FIG. 5 illustrates an example flowchart for collecting breast milk and/or colostrum. The process of the flowchart may be performed using the collection device and/or breast pump depicted in FIGS. 1-4. Alternatively, another device may be configured to perform one or more of the following acts. Additional, fewer, or different acts may be included.

At act S101, a collection device is placed over a nipple of a breast. In the placement of the collection device, the breast is inserted through the first open end of the breast shield of the collection device, where the interior surface of the breast shield abuts or touches a portion of the breast. Additionally, in the placement, the breast shield is aligned with the nipple of the breast such that the second open end of the breast shield surrounds the nipple.

At act S103, breast milk is expressed from the nipple. This may be done manually by the female wearing the collection device. Alternatively, the breast milk may be expressed by placing a breast pump over the collection tube of the collection device and turning on the breast pump. The breast pump may pull a partial vacuum within the collection tube using a suction transfer apparatus. Alternatively, or additionally, the breast pump may massage the nipple to stimulate the nipple to express the breast milk.

At act S105, breast milk is collected in the collection tube of the collection device. The collection of breast milk may continue until the tube is full, or until enough breast milk or colostrum is collected. Alternatively, the collection process may continue until no additional breast milk is expressed for a fixed period of time (e.g., 5 minutes, 10 minutes).

At act S107, the collection device is removed from the breast. In certain examples, the woman may lean forward while removing the device to avoid spilling the collected breast milk. In one example, the entire collection device is removed. In an alternative example, the collection tube of the device is only removed (e.g., by unscrewing the collection tube from the breast shield). In another example, the entire collection device is removed, and then the collection tube of the device is detached from the breast shield.

At act S109, the collected breast milk may be stored in a separate container, fed to the child, or saved in the detached collection tube. A lid may be placed over the open end of the collection tube to seal the breast milk contents therein. To the extent the breast milk is transferred into a separate container or fed to the child, the transfer may include pouring the breast milk into the container or into the child's mouth. Alternatively, a syringe may be used to transfer the collected breast milk to the container or child's mouth. Not all of the breast milk may be readily extracted by pouring or using a syringe. Several drops may be left behind in the collection tube. In such instances, the collection device (or the detached collection tube) may be inverted, wherein the closed end of the collection tube is moved through the first open end of the breast shield (or the open end of the detached collection tube. This movement may be accomplished with pressure from a finger on the outside of the tube at the closed end. In the inversion process, the interior surface of the collection tube (and possibly the interior surface of the breast shield) is exposed. Remaining drops of breast milk (e.g., colostrum) may be collected, such as with a finger, and fed to the child or added to the separate container.

At act S111, in instances of storing the breast milk in a separate container or feeding the breast milk to the child, the process of collecting breast milk may be repeated, wherein the device is reattached over the nipple of the breast, breast milk is expressed and collected, and the device (or a portion thereof) is removed. This may be an iterative process that is repeated until no additional breast milk is expressed for a fixed period of time (e.g., 5 minutes, 10 minutes).

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, are apparent to those of skill in the art upon reviewing the description.

As used herein, the singular forms "a," "an," and "the" include plural referents unless the context clearly dictates otherwise.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

It is intended that the foregoing detailed description be regarded as illustrative rather than limiting and that it is understood that the following claims including all equivalents are intended to define the scope of the invention. The claims should not be read as limited to the described order or elements unless stated to that effect. Therefore, all embodiments that come within the scope and spirit of the following claims and equivalents thereto are claimed as the invention.

What is claimed is:

1. A collection device comprising:
a breast shield having a first open end, a second open end, and a breast covering material positioned between the first open end and the second open end, wherein an interior surface of the breast shield is configured to abut a portion of a breast inserted through the first open end, wherein the second open end is configured to surround a nipple of the breast, and wherein a diameter of the second open end is less than a diameter of the first open end; and
a collection tube having an open end and a permanently closed end, wherein the open end of the collection tube is configured to connect with the second open end of the breast shield, wherein the collection tube comprises a conical frustum having a height between the open end and the closed end of the collection tube, wherein a diameter at the open end of the collection tube is greater than a diameter at the closed end of the collection tube,
wherein the collection device is configured to collect breast milk in the collection tube through stimulation of the nipple, and
wherein the collection tube is configured to be inverted, wherein the closed end of the collection tube is moved through the open end of the collection tube to expose an interior surface of the collection tube and provide easier access to the breast milk collected in the collection tube.

2. The collection device of claim 1, wherein the breast milk is colostrum.

3. The collection device of claim 1, wherein the collection tube is attachable and detachable from the breast shield.

4. The collection device of claim 3, further comprising:
a safety lid configured to be secured to the open end of the collection tube when the collection tube is detached from the breast shield.

5. The collection device of claim 3, wherein the collection tube is configured to be inverted when detached from the breast shield.

6. The collection device of claim 3, wherein the breast shield comprises a ring-shaped projection having an external surface configured to abut a portion of an internal surface of the collection tube at the open end of the collection tube when attached to the breast shield.

7. The collection device of claim 6, wherein the external surface of the ring-shaped projection is threaded and the portion of the internal surface of the collection tube is threaded such that the collection tube is configured to screw onto the breast shield at the ring-shaped projection.

8. A collection tube configured to attach to a breast shield having a first open end, a second open end, and a breast covering material positioned between the first open end and the second open end, the collection tube comprising:
an open end and a permanently closed end, wherein the open end of the collection tube is configured to attach to and detach from the second open end of the breast shield,
wherein the collection tube comprises a conical frustum having a height between the open end and the closed end of the collection tube, wherein a diameter at the open end of the collection tube is greater than a diameter at the permanently closed end of the collection tube,
wherein the collection tube is configured to collect breast milk when attached to the breast shield through stimulation of the nipple, and
wherein the collection tube is configured to be inverted, wherein the closed end of the collection tube is moved through the open end of the collection tube to expose an interior surface of the collection tube and provide easier access to the breast milk collected in the collection tube.

9. The collection tube of claim 8, further comprising:
a safety lid configured to be secured to the open end of the collection tube when the collection tube is detached from the breast shield.

10. The collection tube of claim 8, wherein the collection tube is configured to be inverted when detached from the breast shield.

11. The collection tube of claim 8, wherein the collection tube is configured to attach to a ring-shaped projection of the breast shield, wherein a portion of an internal surface of the collection tube at the open end of the collection tube is configured to abut an external surface of the ring-shaped projection of the breast shield.

12. The collection tube of claim 11, wherein the portion of the internal surface of the collection tube is threaded such that the collection tube is configured to screw onto the ring-shaped projection.

13. A method of collecting breast milk comprising:
placing a collection device over a nipple of a breast, the collection device comprising (1) a breast shield having a first open end, a second open end, and a breast covering material positioned between the first open end and the second open end, wherein an interior surface of the breast shield abuts a portion of the breast and the second open end is surrounds the nipple of the breast, and (2) a collection tube having an open end and a closed end, wherein the open end of the collection tube is connected to the second open end of the breast shield;
expressing breast milk from the nipple;
collecting the breast milk in the collection tube of the collection device;
removing the collection device from the nipple of the breast;
inverting the collection tube, wherein the closed end of the collection tube is moved through the open end of the collection tube to expose an interior surface of the collection tube and provide easier access to the breast milk collected in the collection tube; and
extracting the breast milk from the inverted collection tube.

14. The method of claim 13, further comprising:
pouring the collected breast milk into a separate storage container or feeding the collected breast milk to a child directly from the collection device.

15. The method of claim 13, wherein the breast milk is expressed from the nipple with a breast pump placed over the collection device.

16. The method of claim 15, wherein the breast pump uses suction to create of a partial vacuum within the collection tube.

17. The method of claim 13, further comprising:
    detaching the collection tube from the breast shield.

18. The method of claim 17, further comprising:
    pouring the collected breast milk from the detached collection tube into a separate storage container or feeding the collected breast milk to a child directly from the detached collection tube.

\* \* \* \* \*